US011464482B2

(12) United States Patent
Hynynen et al.

(10) Patent No.: US 11,464,482 B2
(45) Date of Patent: Oct. 11, 2022

(54) SYSTEM AND METHOD FOR MEASURING AND CORRECTING ULTRASOUND PHASE DISTORTIONS INDUCED BY ABERRATING MEDIA

(71) Applicants: Kullervo Henrik Hynynen, Toronto (CA); Meaghan Anne O'Reilly, Toronto (CA)

(72) Inventors: Kullervo Henrik Hynynen, Toronto (CA); Meaghan Anne O'Reilly, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 684 days.

(21) Appl. No.: 14/772,316

(22) PCT Filed: Mar. 4, 2014

(86) PCT No.: PCT/US2014/020279
§ 371 (c)(1),
(2) Date: Sep. 2, 2015

(87) PCT Pub. No.: WO2014/138050
PCT Pub. Date: Sep. 12, 2014

(65) Prior Publication Data
US 2016/0007954 A1    Jan. 14, 2016

Related U.S. Application Data

(60) Provisional application No. 61/771,992, filed on Mar. 4, 2013.

(51) Int. Cl.
*A61B 8/00* (2006.01)
*A61B 8/15* (2006.01)
(Continued)

(52) U.S. Cl.
CPC .............. *A61B 8/15* (2013.01); *A61B 8/0808* (2013.01); *A61B 8/4494* (2013.01); *A61B 8/481* (2013.01);
(Continued)

(58) Field of Classification Search
None
See application file for complete search history.

(56) References Cited

U.S. PATENT DOCUMENTS

| 5,052,394 A | 10/1991 | Carpenter et al. |
| 5,752,515 A | 5/1998 | Jolesz |

(Continued)

FOREIGN PATENT DOCUMENTS

| CN | 1444491 A | 9/2003 |
| CN | 1449261 | 10/2003 |

(Continued)

OTHER PUBLICATIONS

The International Search Report and Written Opinion dated Jun. 10, 2014 for International Application No. PCT/US2014/020279.
(Continued)

*Primary Examiner* — Patricia J Park
(74) *Attorney, Agent, or Firm* — Quarles & Brady LLP (57) ABSTRACT

A system and method for efficiently transmitting and receiving focused ultrasound through a medium, such as bone, is provided. The focal region of the focused ultrasound is iteratively updated to provide an improved focus through the medium. This method may be carried out using a transducer assembly that includes two or more transmit arrays each operating at a different frequency. An initial focus is set and updated by delivering focused ultrasound with a lower frequency transmit array. The phase corrections determined in the first iteration are applied to subsequently higher frequency transmit arrays and received signals, and the
(Continued)

process repeated until a desired focus or image resolution is achieved.

13 Claims, 4 Drawing Sheets

(51) Int. Cl.
*A61B 8/08* (2006.01)
*A61B 8/06* (2006.01)
*A61N 7/00* (2006.01)

(52) U.S. Cl.
CPC .............. *A61B 8/5269* (2013.01); *A61B 8/06* (2013.01); *A61B 8/0891* (2013.01); *A61B 8/5207* (2013.01); *A61B 8/54* (2013.01); *A61N 2007/0021* (2013.01); *A61N 2007/0039* (2013.01); *A61N 2007/0052* (2013.01); *A61N 2007/0078* (2013.01)

(56) References Cited

U.S. PATENT DOCUMENTS

| | | | |
|---|---|---|---|
| 6,612,988 | B2 | 9/2003 | Maor |
| 8,002,705 | B1* | 8/2011 | Napolitano ......... G01S 7/52019 |
| | | | 600/437 |
| 2003/0092987 | A1* | 5/2003 | Hynynen ............. A61B 8/0858 |
| | | | 600/437 |
| 2004/0006272 | A1 | 1/2004 | Vortman |
| 2004/0210134 | A1 | 10/2004 | Hynynen et al. |
| 2005/0251043 | A1* | 11/2005 | Saied ....................... A61B 8/10 |
| | | | 600/443 |
| 2006/0241462 | A1 | 10/2006 | Chou |
| 2007/0167752 | A1* | 7/2007 | Proulx ................ G01S 7/52095 |
| | | | 600/437 |
| 2008/0297282 | A1* | 12/2008 | Larson, III ............ H01L 41/107 |
| | | | 333/195 |
| 2009/0156939 | A1 | 6/2009 | Sadaka |
| 2010/0094133 | A1 | 4/2010 | Yoshiara et al. |
| 2011/0098568 | A1 | 4/2011 | Someda et al. |
| 2011/0301467 | A1* | 12/2011 | Miller .................. A61B 8/4477 |
| | | | 600/459 |
| 2011/0319793 | A1* | 12/2011 | Hynynen ................. A61N 7/02 |
| | | | 601/2 |
| 2012/0226164 | A1* | 9/2012 | Tashiro ................ A61B 8/0841 |
| | | | 600/461 |

FOREIGN PATENT DOCUMENTS

| | | |
|---|---|---|
| CN | 201200425 Y | 3/2009 |
| CN | 102057297 A | 5/2011 |

OTHER PUBLICATIONS

European Patent Office Extended Search Report for application 14760248.6 dated Jan. 13, 2017, 10 pages.
European Patent Office Partial Search Report for application 14760248.6 dated Sep. 27, 2016, 8 pages.
Haworth, Kevin J., et al. "Towards aberration correction of transcranial ultrasound using acoustic droplet vaporization." Ultrasound in medicine & biology 34.3 (2008): 435-445.
O'Reilly, M.A. et al. "A PVDF Receiver for Ultrasound Monitoring of Transcranial Focused Ultrasound Therapy," IEEE Transactions on Biomedical Engineering, 2010; 57(9):2286-2294.
Aubry JF, et al. Experimental demonstration of noninvasive transskull adaptive focusing based on prior computed tomography scans. Journal of the Acoustical Society of America. 2003; 113(1):84-93.
Clement GT, et al. A non-invasive method for focusing ultrasound through the human skull. Physics in Medicine and Biology. 2002;47(5):1219-1236.
Gateau J, et al. Transcranial ultrasonic therapy based on time reversal of acoustically induced cavitation bubble signature. IEEE Trans Biomed Eng. 2010;57(1):134-144.
Canadian Intellectual Property Office. Office action for application 2,898,503, dated Feb. 28, 2020. 3 pages.

* cited by examiner

SYSTEM AND METHOD FOR MEASURING AND CORRECTING ULTRASOUND PHASE DISTORTIONS INDUCED BY ABERRATING MEDIA

CROSS-REFERENCE TO RELATED APPLICATIONS

This application represents the U.S. National Stage of International Application No. PCT/US2014/020279, filed Mar. 4, 2014 which claims the benefit of U.S. Provisional Patent Application Ser. No. 61/771,992, filed on Mar. 4, 2013, and entitled "System and Method for Measuring and Correcting Ultrasound Phase Distortions Induced by Aberrating Media."

STATEMENT REGARDING FEDERALLY SPONSORED RESEARCH

This invention was made with government support under EB003268 and EB009032 awarded by the National Institutes of Health. The government has certain rights in the invention.

BACKGROUND OF THE INVENTION

The field of the invention is systems and methods for focused ultrasound ("FUS"). More particularly, the invention relates to systems and methods for efficiently transmitting focused ultrasound through aberrating media, including skull bone and other tissues that may aberrate ultrasound.

Transcranial focused ultrasound surgery has been clinically investigated for the non-invasive treatment of brain disorders, including chronic pain, essential tremor, and primary brain tumors. Although it is an attractive modality for imaging and therapy in the brain, transcranial ultrasound suffers from the poor propagation of ultrasound through the skull bone, which attenuates and aberrates the beam. At low frequencies, the phase aberrations that result from the heterogeneous and irregular nature of the skull bone are minimal, while at high frequencies phase corrections are required to achieve an ultrasound focus in the brain. The necessary phase delays for these corrections can be determined from computer simulations of the sound propagation through the skull bone, using geometry and bone density information obtained from preoperative computed tomography scans. Even the simplest computational models, however, can take several hours to compute the phase delays.

A simple direct method for measuring phase delays through an aberrator is to place an ultrasound source at the focus and use time-of-flight measurements to calculate the phase delays between transducer elements. Noninvasive realizations of this technique have used bubbles inside the skull cavity as the sound beacon, with the bubbles either induced through acoustic droplet vaporization or transient cavitation. In one study by Gateau et al., computed tomography-based phase correction was utilized for an initial focusing step and then bubble signature-based phase corrections were used to improve the transducer array focusing and to conduct beam steering. The frequency of the transducer array used by Gateau, et al., was 1 MHz, which was too high to create a cavitation event without first using the simulation based phase correction. In addition, the receivers were a subset of the transmit elements, and were sensitive primarily at their driving frequency.

In a study by Haworth, et al., it was proposed that bubble-based phase correction could be performed by first sonicating at low frequencies and then using harmonic imaging to calculate the phase delays and refocus at the higher frequency. A device and strategy to perform such phase corrections, however, were not described. In particular, it has not been addressed that bubble activity at the low frequency could occur anywhere within a fairly large transmit focal zone, which could compound targeting errors.

It would therefore be desirable to provide a system and method for efficiently transmitting focused ultrasound through a medium, such as bone.

SUMMARY OF THE INVENTION

The present invention overcomes the aforementioned drawbacks by providing a system and method for efficiently transmitting focused ultrasound through a medium, such as bone, using an adaptive focusing scheme. The focal region of the focused ultrasound is iteratively updated to provide an improved focus through the medium. This method may be carried out using a transducer assembly that includes two or more transmit arrays each operating at a different frequency. An initial focus is set and updated by delivering focused ultrasound with a lower frequency transmit array. The phase corrections determined in the first iteration are applied to subsequently higher frequency transmit arrays and the process repeated until a desired focus is achieved.

It is an aspect of the invention to provide a method for adjusting a focus of a focused ultrasound beam. An initial focal region of an ultrasound transducer assembly having a plurality of transmit arrays each having a different operating frequency is defined by setting an initial focus of the transmit arrays. Ultrasound energy is delivered to the initial focal region to excite a contrast agent present in the initial focal region using one of the plurality of transmit arrays. Signals responsive to the excited contrast agent in the initial focal region are then received using the ultrasound transducer array. An image is produced from the received signals, and a center of the initial focal region is determined from this image. Phase correction values are computed using the determined center of the initial focal region, and are applied to the focused ultrasound transducer assembly to update the initial focus, thereby defining an updated focal region that is more focused than the initial focal region. This process is iteratively repeated until the updated focal region corresponds to a desired focus. During each repetition of this process, ultrasound energy is delivered to the updated focal region to excite a contrast agent present in the updated focal region using a different one of the plurality of transmit arrays that operates at a higher frequency than the previous transmit array.

It is another aspect of the invention to provide a transducer assembly for use with a focused ultrasound system. The transducer assembly includes a plurality of integrated transducer units and a multiplexing circuit in communication with the integrated transducer units. Each integrated transducer unit includes at least two transducer elements that are concentrically nested to form the integrated transducer unit. The multiplexing circuit is configured to connect the transducer elements in each integrated transducer unit to at least one of a transmit line and a receive line.

It is another aspect of the invention to provide a focused ultrasound system that includes a transducer assembly and a processor in communication with the transducer assembly. The transducer assembly includes a plurality of transducer arrays each composed of transducer elements, each transducer array operating at a different frequency. The transducer assembly may include at least one additional receive array composed of receive transducer elements. The processor is configured to set a focal region for the transducer assembly and to iteratively update this focal region for each transmit array in the transducer assembly. In each iteration, the processor selects the transmit array having the lowest remaining operating frequency and directs the selected transmit array to excite the initial focal region for that transmit array and directs the at least one receive array to receive signals from the initial focal region. The processor then reconstructs an image of the focal region from the received signals and computes phase correction values from the reconstructed image. The processor then applies the computed phase correction values to the selected transmit array and to the transmit array having the next highest operating frequency.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A system and method for efficiently transmitting focused ultrasound through skull bone using a focused ultrasound ("FUS") system is provided. Particularly, an ultrasound transducer array design and a method for adaptive ultrasound focusing through the skull bone are provided.

Figure 1:
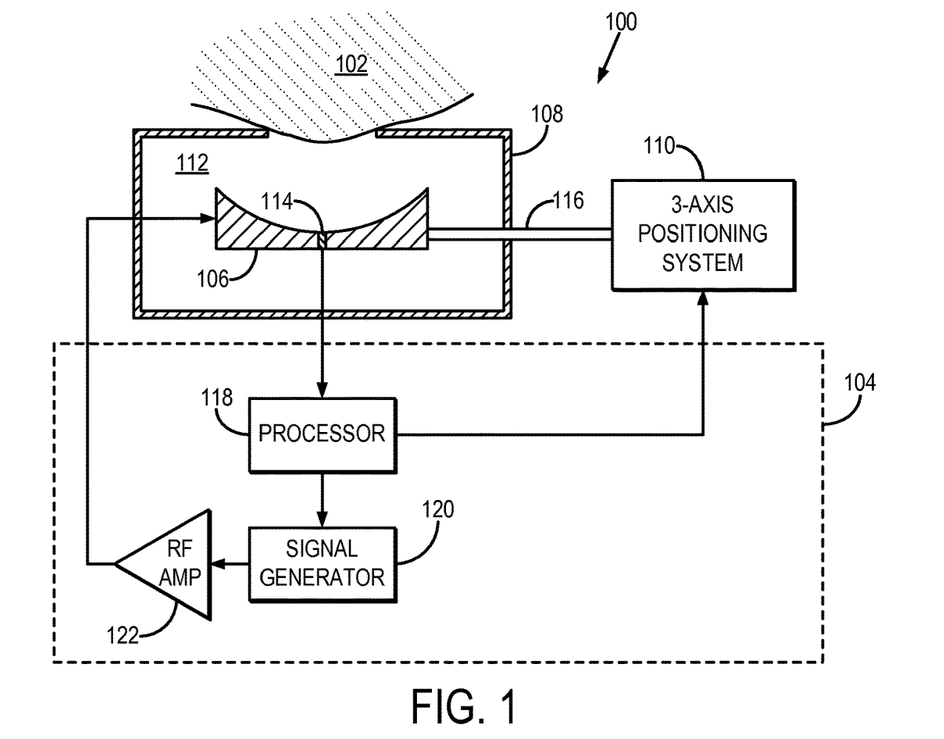
FIG. 1 is a block diagram of an example of a focused ultrasound system.

Referring to FIG. 1, an exemplary focused ultrasound ("FUS") system 100 for delivering focused ultrasound to a subject 102 is illustrated. The FUS system includes a controller 104, an ultrasound transducer 106, an enclosure 108, and a positioning system 110. The enclosure 108 houses the ultrasound transducer 106 and provides an interface with the subject 102 such that ultrasound energy can be efficiently transferred from the ultrasound transducer 106 to the subject 102. By way of example, the enclosure 108 may be filled with an acoustic coupling medium 112, which allows for a more efficient propagation of ultrasound energy than through air. Exemplary acoustic coupling media 112 include water, such as degassed water. Advantageously, the ultrasound transducer 106 includes a signal detector 114, such as a hydrophone. By way of example, the signal detector 114 may include a wideband polyvinylidene fluoride ("PVDF") hydrophone, such as those described by M. A. O'Reilly and K. Hynynen in "A PVDF Receiver for Ultrasound Monitoring of Transcranial Focused Ultrasound Therapy," IEEE Transactions on Biomedical Engineering, 2010; 57(9):2286-2294. The ultrasound transducer 106 is coupled to the positioning system 110 by way of a support 116. The positioning system 110 is advantageously a three-axis positioning system that provides precise and accurate positioning of the ultrasound transducer 106 in three dimensions, but can be, in general, a multi-axis positioning system that provides precise and accurate positioning of the ultrasound transducer 106 in two or more dimensions or directions.

The controller 104 generally includes a processor 118, a signal generator 120, and a radio frequency ("RF") amplifier 122. The signal generator 120 may include, for example, a function generator, and is configured to provide a driving signal that directs the ultrasound transducer 106 to generate ultrasound energy. The driving signal produced by the signal generator 120 is amplified by the RF amplifier 122 before being received by the ultrasound transducer 106. When the FUS system 100 is used during a magnetic resonance guided FUS ("MRgFUS") application, the controller 104 can be positioned inside or outside of the magnet room of the magnetic resonance imaging ("MRI") system.

The processor 118 is in communication with the signal generator 120 and directs the signal generator 120 to produce the driving signal that is delivered to the ultrasound transducer 106. As will be described below in detail, the processor 118 may be configured to adjust properties of the driving signal such that the ultrasound energy pressure produced by the ultrasound transducer 106 is adjusted in accordance with embodiments of the present invention.

The processor 118 receives acoustic signals from the signal detector 114. As will be described below in detail, the feedback information provided by the signal detector 114 is utilized by the processor 118 to direct the appropriate adjustments in ultrasound energy. The processor 118 is also in communication with the positioning system 110, and is configured to direct the positioning system 110 to move the position of the ultrasound transducer 106 during a sonication procedure. In the case that the ultrasound transducer 106 is a phased array transducer, the controller 104 may adjust the phase and/or amplitude of the driving RF signal to each transducer element to control the location of the focal spot.

In general, the ultrasound transducer 106 may be referred to as a transducer assembly that includes one or more arrays of ultrasound transducer elements. Each transducer array may include only transmit elements, only receive elements, or both transmit and receive elements. By way of example, the transducer assembly may include multiple integrated transmit and receive arrays. For instance, the transducer assembly may include two or more transmit arrays operating at different frequencies, and one or more receive arrays with resonances at harmonics or sub-harmonics of the transmit arrays. Preferably, the transducer assembly would be a full hemisphere to provide the best focusing capabilities. All of the arrays can be either fully populated or sparse if a reduced number of transducer elements is preferred.

Figure 2A:
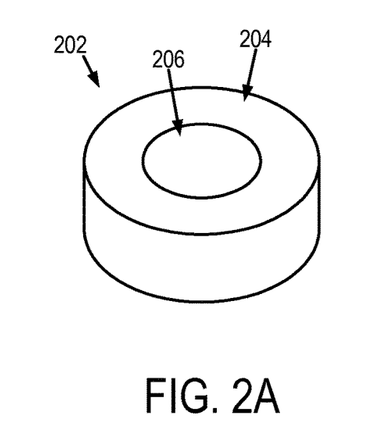
FIG. 2A is an example of an integrated transducer unit that includes a nested transmit transducer and receive transducer.
Figure 2B:
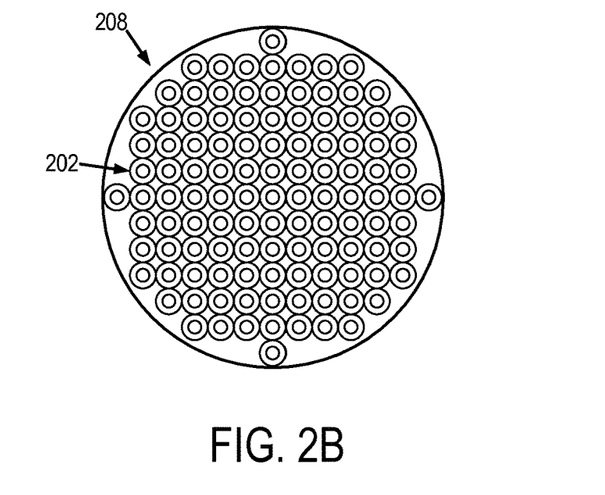
FIG. 2B is an example of an array of integrated transducer units.

In one configuration, such as the one illustrated in FIGS. 2A and 2B, the transducer assembly 208 is composed of integrated units 202 that contain a transmit element 204 and a receive element 206. The transmit element 204 and receive element 206 are arranged in the integrated unit 202 such that they are coaxial. For example, the transmit element 204 can be a circular transducer element nested inside an annular-shaped receive element 206. Although FIGS. 2A and 2B depict integrated units 202 composed of only two transducer elements, it is noted that the integrated units 202 may also be constructed to include more than two nested transducer elements, each capable of transmission, reception, or both. The integrated units 202 can be arrayed over the extent of the transducer assembly 208, as illustrated in FIG. 2B. In general, the frequency of the integrated units 202 would increase from the exterior transducer elements of the integrated units 202 to the interior transducer elements of the integrated units 202 so as to keep good directivity at higher frequencies. The lowest transmit ultrasound frequency is preferably around 100-300 kHz, where distortions due to the skull are minimal.

Figure 2C:
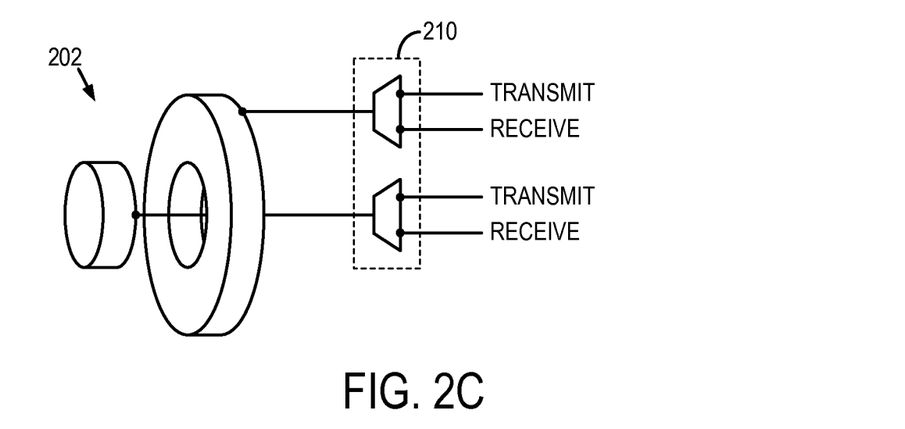
FIG. 2C is an example of a multiplexing circuit connected to an integrated transducer unit.
Figure 2D:
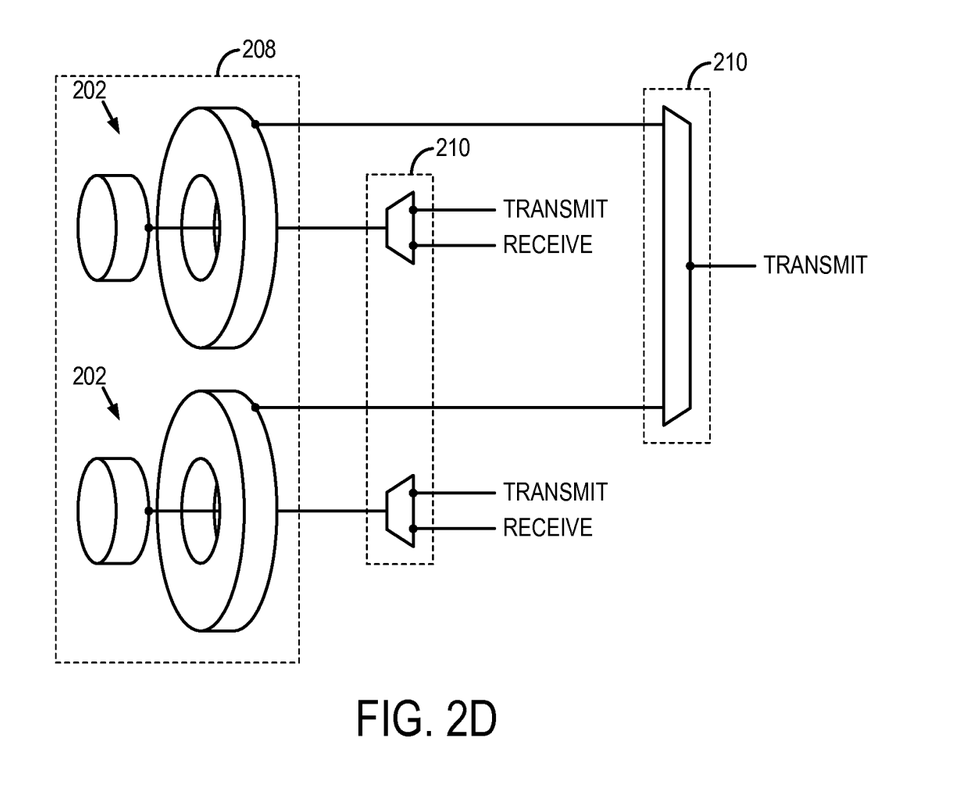
FIG. 2D is another example of a multiplexing circuit connected to integrated transducer units.

With reference to FIGS. 2C and 2D, the nested transducer elements in the integrated units 202 are connected to multiplexers in a multiplexer circuit 210 that can, under the direction of a controller, connect the RF-transmit signal to any of the transducer elements capable of transmitting ultrasound energy. Similarly, the multiplexers can connect the receiver electronics to any of the transducer elements that are capable of detecting acoustic signals. It is possible also to connect multiple transducer elements simultaneously to separate transmit and/or receive lines. Two example configurations of the possible connections between integrated transducer units 202 and the multiplexing circuit 210 are illustrated in FIGS. 2C and 2D. In FIG. 2C, each transducer element in the each integrated transducer unit 202 is connected to a multiplexer that connects that transducer element to both a transmit line and a receive line. In FIG. 2D, each integrated transducer unit 202 includes one transducer element that, via the multiplexing circuit, is connected only to a transmit line and one transducer element that, via the multiplexing circuit 210, is connected to both the transmit line and a receive line. It should be appreciated that any suitable combination of connections between transducer elements in the integrated transducer units 202 and the transmit and receive lines can be made via an appropriately configured multiplexing circuit. It is also noted that each integrated transducer unit 202 does not need to be connected to the transmit and receive lines in the same manner; rather, one group of integrated transducer units 202 could be connected to the transmit and receive lines in one configuration (e.g., the configuration shown in FIG. 2C) while another group of integrated transducer units 202 could be connected to the transmit and receive lines in another configuration (e.g., the configuration shown in FIG. 2D).

Figure 3:
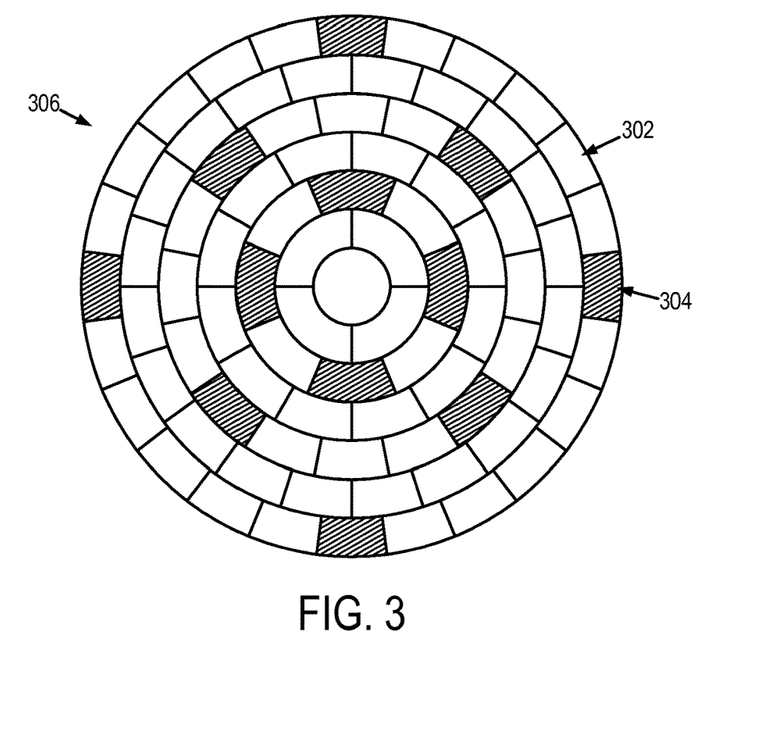
FIG. 3 is an example of a transducer assembly that includes sparsely distributed receive transducer elements.

Referring now to FIG. 3, the transmit elements 302 and the receive elements 304 of a transducer assembly 304 can also be interspersed in a sparse arrangement over the entire array aperture. In some high power applications there is a need for a large number of transmit elements, however a substantially smaller number of receive elements are necessary to map the contrast agent activity. To reduce the hardware requirements, the receiver elements or integrated units could be more sparsely populated within the larger number of transmit elements. Phase delays calculated from the receive elements could then be applied to groups of surrounding transmit elements that would be propagating sound through the same region of the skull bone.

Figure 4:
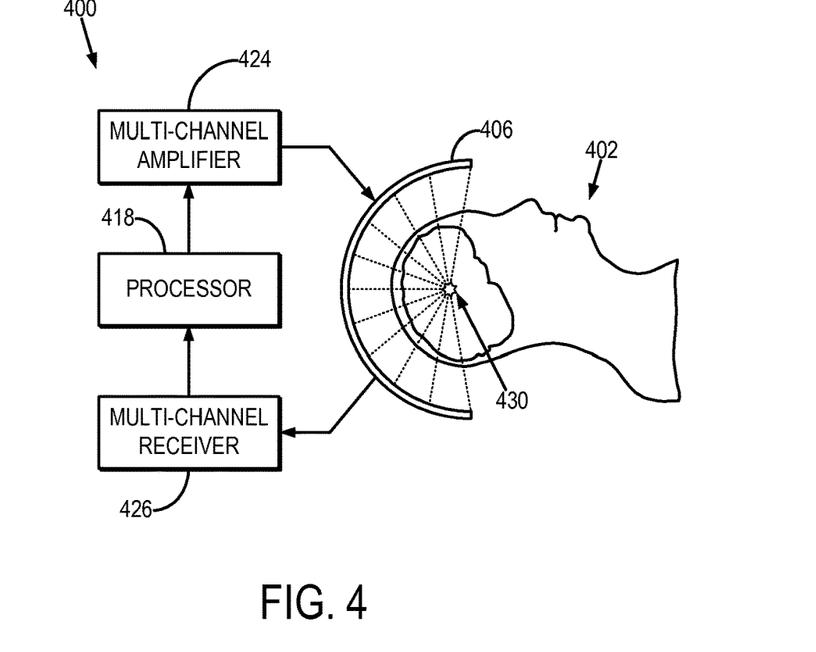
FIG. 4 is a block diagram of an example of a focused ultrasound system configured for transcranial applications.

Referring now to FIG. 4, in some instances, an FUS system 400 may be configured more particularly for transcranial ultrasound applications in human subjects. In such a system, a subject 402 receives ultrasound energy from a transducer 406 that is configured to surround an extent of the subject's head. For example, the transducer 406 may be an approximately hemispherical array of transducer elements. The FUS system 400 may include a cooling system, such as a sealed water system with an active cooling and degassing capacity, so that an appropriate temperature of the skull and skin of the subject 402 may be maintained during treatment.

The FUS system 400 includes a processor 418 that is in communication with a multi-channel amplifier 424 and a multi-channel receiver 426. The multi-channel amplifier 424 receives driving signals from the processor 418 and, in turn, directs the transducer elements of the transducer 406 to generate ultrasound energy. The multi-channel receiver 426 receives acoustic signals during sonications and relays these signals to the processor 418 for processing in accordance with embodiments of the present invention. The processor 418 may also be configured to adjust the driving signals in response to the acoustic signals received by the multi-channel receiver 426. For example, the phase and/or amplitude of the driving signals may be adjusted so that ultrasound energy is more efficiently transmitted through the skull of the subject 402 and into the target volume-of-interest 430. Furthermore, the acoustic signals may also be analyzed to determine whether and how the extent of the focal region should be adjusted.

Figure 5:
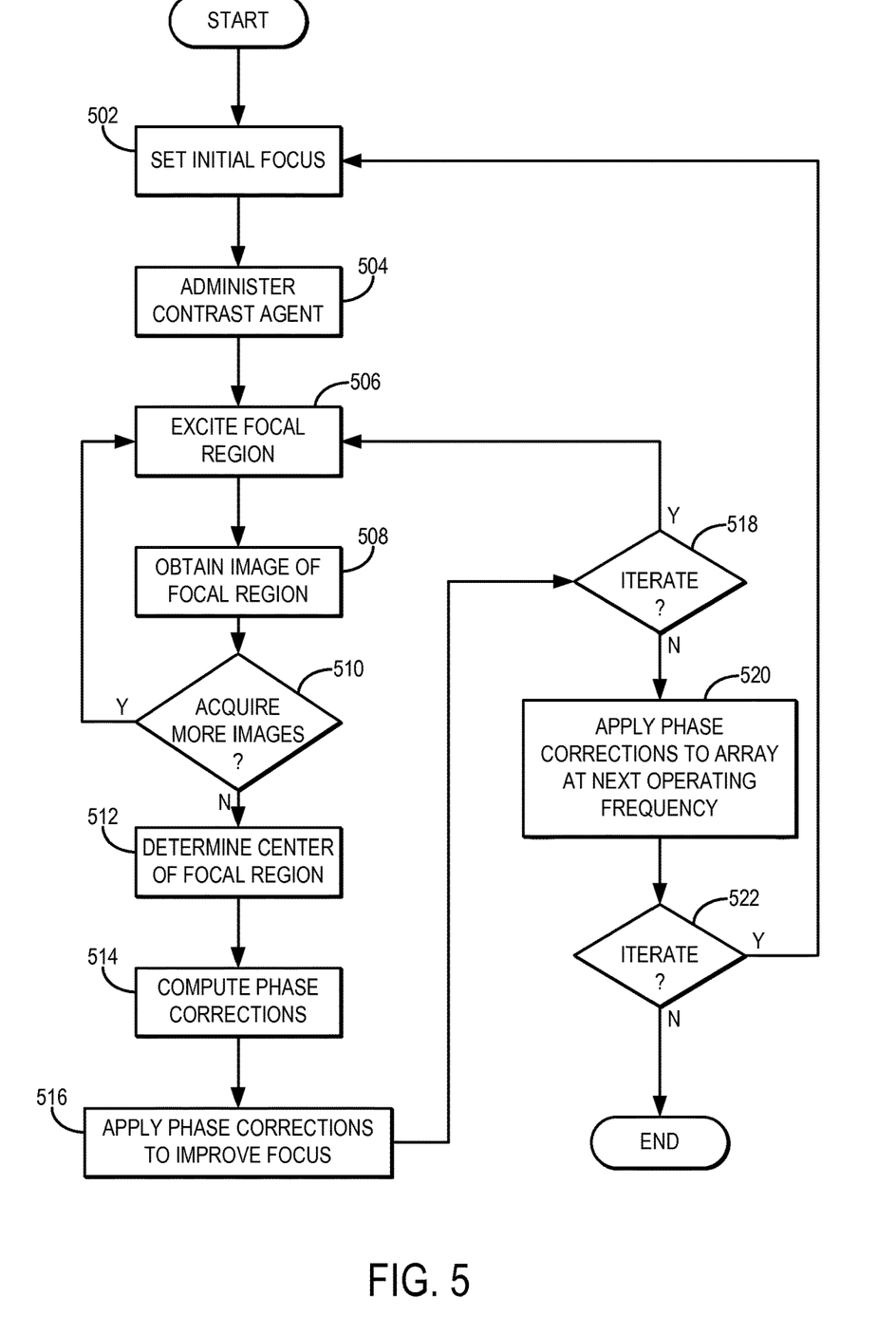
FIG. 5 is a flowchart setting forth the steps of an example of a method for adaptively adjusting the focus of a transducer assembly that includes two or more transmit arrays operating at different frequencies.

Having described the general structure of a FUS system that implements the present invention, reference is now made to FIG. 5, which illustrates a flowchart setting forth the steps of an example of a method for improving the transmission efficiency of delivering focused ultrasound through skull bone or other bony structures. This example method is described with respect to a transcranial application as follows.

Using geometric focusing, and ignoring the skull contributions, the ultrasound would be initially focused in the brain using lower frequency ultrasound, as illustrated at step 502. This initial focus would be relatively large due to the low frequency used. The patient may then be administered an ultrasound contrast agent, as illustrated at step 504. This ultrasound contrast agent may be either a microbubble contrast agent or a phase-change droplet contrast agent, and is preferably administered at a very low concentration. For instance, the contrast agent concentration can be sufficiently low as to be able to image individual bubbles in the vasculature.

The low frequency transmit array is then used to excite the individual bubbles, as indicated at step 506. Harmonic emissions that are responsive to this excitation are acquired by one of the receive arrays and beamformed using both phase and amplitude information to produce an initial image of the bubble, as indicated at step 508. The initial beamforming considers only geometric delays and not those produced by the skull. As indicated at decision block 510, the excitation and image reconstruction steps are repeated to create a time series of images depicting bubble activity at the transmit focus. To the extent that additional contrast agent is required, more contrast agent will be administered to the subject.

By examining the spatial extent of the activity and the strength of the bubble responses, the approximate center of the transmit focus can be determined from the time series of images, as indicated at step 512. Using the emissions from one of the bubble events at this location, phase corrections for the transmitted and received beams are calculated, as indicated at step 514. These phase corrections are then applied to the transmit elements to improve the transmit focus, as indicated at step 516. This process can optionally be repeated to improve the estimates of the transmit and receive phase corrections, as indicated at decision block 518.

The phase corrections could then be applied to the transmit array with the next lowest frequency, creating a time series of images with the corresponding receiver array to determine the spatial extent of the transmit focus and to fine-tune the transmit and receive focusing, as indicated at step 520. This process could be iterated at each transmit frequency, and repeated at increasing frequencies to create a sharp treatment focus at high frequencies, as indicated at decision block 522.

In some embodiments, when the bubble signatures recorded at the receivers are very weak, the image quality may be improved by fitting the expected bubble response to the raw data. One implementation of this may include finding an optimal fit by cross-correlating a template of the expected bubble response to the raw data on each line. Thus, in some embodiments the systems and methods of the present invention include providing one or more templates of expected bubble response. Data captured at a low sampling frequency could be up-sampled prior to fitting the template in order to preserve position information.

The present invention provides the ability to perform high resolution vascular mapping of the brain for diagnostic purposes. This can be accomplished by scanning the transmit focus throughout the brain while collecting the scattered signals from microbubbles that are infused into the blood vessels. In this instance, the transmit and receive signal corrections are derived first and then the three-dimensional images of the bubbles (and thus the vasculature) are formed and tracked as a function of time. For this imaging, either standard short ultrasound imaging bursts can be used to provide time-resolved echo location, or long ultrasound imaging bursts using the method described above can be used to form the images. The method of the present invention can also improve ultrasound imaging in other aberrating media, including the breast, the heart, the prostate, and so on. Breast imaging, for example, could be conducted with a similar hemispherical array design as would be used for brain imaging and therapy applications.

The present invention has been described in terms of one or more preferred embodiments, and it should be appreciated that many equivalents, alternatives, variations, and modifications, aside from those expressly stated, are possible and within the scope of the invention.

The invention claimed is:

1. A focused ultrasound system, comprising:
   a transducer assembly that includes:
      a plurality of transmit arrays composed of transmit transducer elements, each transmit array operating at a different operating frequency, the plurality of transmit arrays being arranged in a hemispherical array such that the operating frequency of each transmit array increases from an exterior of the hemispherical array to an interior of the hemispherical array;
      at least one receive array composed of receive transducer elements;
      wherein each transmit transducer element comprises a cylindrical annular transducer element;
      wherein each receive transducer element comprises a cylindrical transducer element coaxial with and nested within one of the transmit transducer elements;
      wherein the receive transducer elements are sparsely distributed among the hemispherical array;
   a processor in communication with the transducer assembly and configured to:
      set a focal region for the transducer assembly;
      iteratively update the focal region for each transmit array in the transducer assembly by:
         (a) selecting the transmit array having a lowest remaining operating frequency;
         (b) directing the selected transmit array to excite an initial focal region for that transmit array;
         (c) directing the at least one receive array to receive signals from the initial focal region;
         (d) reconstructing an image of the focal region from the received signals;
         (e) computing phase correction values from the reconstructed image;
         (f) applying the computed phase correction values to the selected transmit array; and
         (g) repeating steps (a)-(f) individually for each transmit array having successively higher operating frequencies until the focal region for each transmit array has been adaptively updated, wherein the computed phase correction values from a previous iteration of step (f) are applied to the transmit array having a next highest operating frequency before directing that transmit array to excite the initial focal region for that transmit array.

2. The focused ultrasound system as recited in claim 1 further comprising a multiplexing circuit in communication with the transducer assembly and configured to allow switching between the plurality of transmit arrays and the at least one receive array.

3. The focused ultrasound system as recited in claim 1 in which each transmit transducer element corresponds one-to-one with a receive transducer element, and each transmit transducer element and receive transducer element pair form an integrated transducer unit.

4. The focused ultrasound system as recited in claim 1 in which the processor is further configured to:
   apply the computed phase correction values to the received signals to form phase-corrected signals; and
   reconstruct an image from the corrected signals.

5. The focused ultrasound system as recited in claim 4 in which the processor is configured to scan the focal region of the transducer assembly through a volume-of-interest while receiving signals from the volume-of-interest.

6. The focused ultrasound system as recited in claim 4 in which the processor is configured to set multiple simultaneously produced focal regions for the transducer assembly so as to accelerate data acquisition.

7. A method for adjusting a focus of a focused ultrasound beam transmitted through an aberrating media, the method comprising:
   a) defining an initial focal region of an ultrasound transducer assembly having a plurality of transmit arrays each having a different operating frequency by setting an initial focus of the transmit arrays, wherein the plurality of transmit arrays in the transducer assembly are arranged in a hemispherical array such that the operating frequency of each transmit array increases from an exterior of the hemispherical array to an interior of the hemispherical array, wherein each transmit transducer element in the ultrasound transducer assembly comprises a cylindrical annular transducer element, each receive transducer element in the ultrasound transducer assembly comprises a cylindrical transducer element coaxial with and nested within one of the transmit transducer elements, and the receive transducer elements are sparsely distributed among the ultrasound transducer assembly;

b) delivering ultrasound energy to the initial focal region to excite a contrast agent present in the initial focal region using one of the plurality of transmit arrays;
c) receiving signals responsive to the excited contrast agent in the initial focal region using the ultrasound transducer assembly;
d) producing an image from the received signals;
e) determining a center of the initial focal region from the produced image;
f) computing phase correction values using the determined center of the initial focal region;
g) applying the computed phase correction values to the focused ultrasound transducer assembly to update the initial focus, thereby defining an updated focal region that is more focused than the initial focal region;
h) repeating steps b)-g) until the updated focal region corresponds to a desired focus, during each repetition delivering ultrasound energy to the updated focal region to excite a contrast agent present in the updated focal region using a different one of the plurality of transmit arrays that operates at a higher frequency than the previous transmit array.

8. The method as recited in claim 7 further comprising:
i) forming phase-corrected signals by applying the phase correction values computed in step f) to the signals received in step c); and
j) and reconstructing an image from the phase-corrected signals.

9. The method as recited in claim 8 in which the aberrating media is a skull bone and the image reconstructed from the phase-corrected signals is a high resolution image that depicts vasculature.

10. The method as recited in claim 9 in which step b) includes delivering the ultrasound energy to the initial focal region to excite a contrast agent present in a concentration that is sufficiently low such that the signals received in step c) are spatially separate and each correspond to a single microbubble in the contrast agent.

11. The method as recited in claim 10 in which steps b)-j) are repeated over a duration of time such that a plurality of time-resolved images that depict microbubble movement caused by blood flow are reconstructed in step j).

12. The method as recited in claim 11 further comprising forming at least one of a dynamic blood flow map and a perfusion map using the plurality of time-resolved images reconstructed in step j).

13. The focused ultrasound system as recited in claim 1 in which the lowest remaining operating frequency is a frequency in a range between 100 kilohertz (kHz) to 300 kHz.

* * * * *